(12) United States Patent
Rich

(10) Patent No.: US 12,263,364 B2
(45) Date of Patent: Apr. 1, 2025

(54) FINE PARTICLE POLLUTION FILTERING FACE MASK SUITABLE FOR AEROBIC EXERCISE

(71) Applicant: Jason Nicholas Rich, Yarrow Point, WA (US)

(72) Inventor: Jason Nicholas Rich, Yarrow Point, WA (US)

(73) Assignee: Jason Rioh, Yarrow Point, WA (US)

( * ) Notice: Subject to any disclaimer, the term of this patent is extended or adjusted under 35 U.S.C. 154(b) by 115 days.

(21) Appl. No.: 17/966,843

(22) Filed: Oct. 16, 2022

(65) Prior Publication Data

US 2024/0123267 A1    Apr. 18, 2024

(51) Int. Cl.
*A62B 23/00*   (2006.01)
*A61L 9/014*   (2006.01)
*A62B 18/10*   (2006.01)
*A62B 23/02*   (2006.01)
*B01D 46/00*   (2022.01)
*B01D 46/52*   (2006.01)

(52) U.S. Cl.
CPC ............ *A62B 23/025* (2013.01); *A61L 9/014* (2013.01); *A62B 18/10* (2013.01); *B01D 46/0032* (2013.01); *B01D 46/521* (2013.01); *A61L 2209/14* (2013.01)

(58) Field of Classification Search
CPC ....... A62B 23/025; A62B 18/10; A61L 9/014; A61L 2209/14; B01D 46/0032; B01D 46/521

See application file for complete search history.

(56) References Cited

U.S. PATENT DOCUMENTS

| | | | | |
|---|---|---|---|---|
| 6,119,691 A | * | 9/2000 | Angadjivand | D04H 1/43838 55/DIG. 35 |
| 2001/0015205 A1 | * | 8/2001 | Bostock | A41D 13/1161 128/206.19 |
| 2006/0130841 A1 | * | 6/2006 | Spence | A41D 13/1107 128/206.19 |
| 2012/0060843 A1 | * | 3/2012 | Magidson | A41D 13/1146 128/206.19 |
| 2015/0173436 A1 | * | 6/2015 | Tsuei | A41D 13/1115 2/424 |
| 2021/0316165 A1 | * | 10/2021 | Wu | A62B 23/025 |
| 2022/0126130 A1 | * | 4/2022 | Zhang | A41D 13/113 |

* cited by examiner

*Primary Examiner* — Steven O Douglas

(57) ABSTRACT

A unique filtering face-piece respirator or mask that is constructed of filtration media capable of sub-micron particle absorption or filtration. Utilizing existing and broadly available low cost media, the mask is patterned from a single sheet of material. It is constructed in a manner that creates an adequate seal as it fits snugly to the user's face, creates structure to ensure a low volume air gap, and deploys unique vertical pleats to increase surface area in order to decrease pressure drop across the mask. Specifically, the design enables the user to inhale and exhale with a pressure drop below 0.4 inches of water at elevated breathing rates of up to 110 liters per hour. Valve design and positioning enable more than 90% of used air to be exited the mask. Meeting these criteria, the mask is intended to be a low cost solution that provides protection from virus, air pollution, or other pathogens with little restriction, allowing subjectively 'comfortable' usage during sports and other highly aerobic activities.

10 Claims, 5 Drawing Sheets

FINE PARTICLE POLLUTION FILTERING FACE MASK SUITABLE FOR AEROBIC EXERCISE

CROSS REFERENCE TO RELATED APPLICATION

Not applicable.

STATEMENT OF FEDERALLY SPONSORED RESEARCH OR DEVELOPMENT

Not applicable

CLASSIFICATIONS

A62B23/025 Filters for breathing protection purposes for respirators the filter having substantially the shape of a mask
A62B18/025 Half Mask

APPLICATION DATA SHEET

Filed separately.

BACKGROUND OF THE INVENTION

Field of the Invention

The present invention relates to face masks that serve to filter viruses, fine air pollutants, and other pathogens. These are defined as the pathogens and pollutants most harmful to humans below 2.5 micrometers in diameter. In particular, the present invention addresses the need for a fine particle mask with low enough restriction to inhalation and exhalation through the filter media to be suitable for sustained aerobic exercise. The pleated construction allows for mass production using a variety of commercially available N95 class filtration media, making the invention suitable for low cost, disposable masks. This low restriction mask is also appropriate in situations where a mask must be worn for extended periods of time and greater degrees of comfort are desired.

Background Art

The COVID-19 global pandemic has driven increased interest in high efficiency masks since early 2020. In addition to COVID, air quality is a major problem in emerging markets due to industrial pollution and an increasing concern in the developed world due to wildfires and other sources. Masks capable of sub-micron particle filtration are frequently used in environments where air quality has become a concern for human health to enable normal outside activities. To reach higher levels of filter efficiency required to remove fine particles, more or thicker layers of filter material are typically used. If the filter area is held constant the addition of more layers of filter material raises the pressure drop across a mask.

A wide variety of solutions have emerged and are available on the market. Disposable, effective, low cost solutions exist but have high levels of resistance when the user's rate of breathing is high, making them uncomfortable and inappropriate for exercise. Low restriction designs are available for both athletic and industrial applications, but their cost is high. A problem with the prior art is the lack of a solution that is low cost, low resistance at breathing rates that support aerobic exercise, and effective against fine pollutants. An affordable, low restriction, comfortable, disposable mask that is suitable for aerobic exercise and capable of sub-2.5 micron filtration is needed. The need for a low cost solution is especially acute in emerging markets where high priced solutions are economically unattainable for the majority of the population.

Patented Inventions attempting to improve personal air quality with masks attached to the user's face are numerous and the prior art is extensive. None of these inventions solve all of the Issues required to be an affordable and efficient mask suitable for aerobic exercise or other forms of high physical exertion where breathing rates are elevated. Provision of high efficiency face masks has been limited by the fact that the thicker filtration layers needed for such performance leave conventionally designated face masks with unacceptable pressure drops or high cost to manufacture.

Some respirators are categorized as being "filtering face-pieces" because the mask body itself functions as the filtering mechanism. Unlike respirators that use rubber or elastomeric mask bodies in conjunction with attachable filter cartridges (examples include U.S. Pat. No. RE39,493 to Yuschak) or insert-molded filter elements (see U.S. Pat. No. 4,790,306 to Braun), filtering face-piece respirators have the filter media comprise much of the whole mask body so that there is no need for installing or replacing a filter cartridge. As such, filtering face-piece respirators are relatively light in weight and easy to use. Examples of patents that disclose filtering face-piece respirators include U.S. Pat. No. 7,131,442 to Kronzer et al., U.S. Pat. Nos. 6,923,182 and 6,041,782 to Angadjivand et al. U.S. Pat. Nos. 6,568,392 and 6,484,722 to Bostock et al., U.S. Pat. No. 6,394,090 to Chen, and U.S. Pat. No. 4,873,972 to Magidson et al.

The concept of a pleated face mask was initially patented by Marcus (U.S. Pat. No. 2,752,916), but the pleats were designed to improve stow-ability on a mask intended to reduce the spread of germs. The invention was inadequate as a fine particulate mask as it cannot be made of materials capable of fine particle filtration, and does not adequately seal to the user's face. Furthermore, the pleats do not aid in reducing restriction. Low cost, disposable face masks suitable for mass production with horizontal pleats was patented by Lutz (U.S. Pat. No. 3,384,227). While the design is not suitable as a pollution mask because it did not support the use if fine particle filtration media and failed to form a seal with the users face, it provided the basis for further improvements.

A better fitting disposable mask was proposed by Bledstien (U.S. Pat. No. 5,701,809). This improved prior art for fit over the nose and controlling the airspace between the users face and the mask. It however, failed to address filtration of fine particles, flow restriction while inhaling, flow restriction while exhaling, and management of moisture within the mask. For these reasons, the invention as proposed by Bledstien is not appropriate to for use during aerobic exercise where fine particulate air pollution is a concern, but is a basis for further improvement.

The National Institute for Occupational Safety and Health applies the "N95" for materials with high filtration of sub-1 micron particles. The filter material of the present invention may be comprised of a number of woven and nonwoven "N95" compliant materials, of one or more layers. There are many commercially available examples of suitable sheet-fiber filter materials capable of sub-micron particle filtration, including microfibers, fibrillated film webs, woven or nonwoven webs, or combinations thereof, comprising, for example, polyolefins, polycarbonates, polyesters, polyurethanes, glass, cellulose or combinations thereof. Electrically charged fibers (U.S. Pat. No. 4,215,682 or US Pat. No. Re 30,782) are especially preferred. 3M Corporation disclosed (in U.S. Pat. No. 6,119,691) filtration media capable of electrostatic absorption of particles well below the micron threshold, which can also be particle loaded for protection from gaseous materials. These are commercially available, low cost, and effective filtration fabrics suitable for disposable pollution masks. These materials, and others similar, are ideal for use in mass production as shapes can be constructed with sewing, heat staking, or adhesion.

To minimize the pressure drop when the user exhales and provide for the near-complete purge of used air and moisture from the mask without disrupting the seal to the face, a one way exhalation valve is fitted to the mask. See U.S. Pat. Nos. 7,028,689, 7,188,622, and 7,013,895 to Martin et al. and U.S. Pat. Nos. 7,117,868, 6,854,463, and 6,843,248 to Japuntich et al., and U.S. Pat. No. RE37,974 to Bowers. The quick removal of exhaled air from the mask interior improves wearer comfort.

The exhalation valve is made separately from the mask body and is subsequently attached to the fibrous media that comprises the mask body. Exhalation valves can be mounted to respirator mask bodies using a variety of techniques. In some respirators, the valve is welded directly to the various layers that comprise the mask body. In other constructions, the valve seat is clamped to the mask body; see U.S. Pat. Nos. 7,069,931, 7,007,695, 6,959,709, and 6,604,524 to Curran et al. additionally, a printed patch of adhesive has been used to secure the exhalation valve to the mask body; see U.S. Pat. No. 6,125,849 to Williams et al. All of these techniques are acceptable for the invention as proposed.

Commercially efficient bonding processes for bonding filtration media were disclosed by 3M Corporation in U.S. Pat. No. 5,078,132. This is one of several viable bonding processes to support the production of the face mask as proposed.

UVEX Corporation (non-patent protected) produces a molded disposable face mask with increased surface area in order to reduce pressure drop across the filtration media. This is achieved through the attachment of external pods to a molded mask. While the solution is effective for filtration of small particles and restriction reduction, the design does not support low cost manufacturing. The product is commercially available, but the complexity of the design and manufacturing requirements mandates a price that is prohibitive for emerging market applications. A molded and assembled product, the design is not similar to the proposed invention.

Folds and pleats are used in several other designs. In most cases they are deployed for fit and not suitable for the thicker media required for fine particle filtration. Three patent filings attempt to use pleats to create a low pressure drop mask suitable for fine particle absorption. U.S. Pat. No. 5,804,295 attempts to reduce the pressure drop with a corrugated filter material, applying a binder to maintain the micro-folds of the corrugation—a fundamentally different approach and construction to the proposed invention. 3M Corporation filed US patents 20090078265 and 20090235934 to define a pleated fine particle mask with low pressure drop. The design deploys horizontal pleats and manages air gaps to the user with a separate structure to form the mask. As described, these inventions are fundamentally different in design and construction than the proposed embodiment.

The present invention is an improvement which avoids the inadequacies of the prior art in numerous kinds of masks. The use of vertical pleats combined with the unique deployment of several other elements of prior art (electrostatic media, multipurpose face mask geometry, exhaust valves, manufacturing methods) provides functional advantages. The construction of the mask allows for a variety of low cost materials and simplified manufacturing methods to be deployed in its creation. The combination of low restriction and low cost are an advantage not currently available in other masks.

OBJECTS OF THE INVENTION

It is an object of this invention to provide an improved face mask that filters fine air pollutants and other pathogens.

It is a further object of this invention to provide a face mask with minimized restriction to inhalation to support various forms of aerobic exercise.

It is a further object of this invention to provide a facemask that can maintain a minimum air space between the face of the user and the mask.

It is a further object of this invention to provide a facemask which allows for the user to exhale directly with minimal retention of warm and used air.

It is a further object of this invention to provide a facemask which minimizes the build-up of moisture during use.

It is a further object of this invention to provide a facemask which seals effectively on the user's face to minimize leakage.

It is a further object of this invention to provide a facemask which directs used air away from the glasses to avoid fogging.

It is a further object of this invention to provide a facemask that is lightweight.

It is a further object of this invention to provide a facemask that can be worn comfortably for extended periods or during exercise.

It is a further object of this invention to provide a facemask that features a large, low restriction exhaust valve directly in line with the user's nose and mouth.

It is a further object of this invention to provide a facemask that filters and captures pollutants of less than 0.3 microns in diameter in accordance with the N95 specification.

It is a further object of this invention to provide a facemask which can be manufactured easily and at low cost.

It is a further object of this invention to provide a facemask to be disposable after single or multiple uses, depending upon the environment.

SUMMARY OF THE INVENTION

The present invention is an improvement in masks covering the wearer's mouth and nose. This mask utilizes materials and methods which, when vertically pleated, provides for a low restriction, snug fitting mask capable of fine particle filtration. Within the scope of the invention, the term "folded" is interchangeable with "pleated." Pleating being defined as a form folding to create overlap and increase total surface area.

The proposed invention is constructed of flat sheet materials capable of achieving the National Institute for Occupational Safety and Health "N95" standard for fine particle filtration. The flat sheet materials are lower cost, but difficult to assemble without additional supports to maintain the structure of the mask. The proposed assembly creates adequate structure through a unique combination of folds, seams, and vertical pleats.

The objects of the invention are realized with a mask comprised of a two sided chamber with a top seam, a bottom seam, and a vertical front fold connecting the two sides of the chamber. The vertical front fold is positioned between the top seam and the bottom seam. The rigidity of the two seams and clip serve to create a cavity and preserve an air gap in front of the user's mouth. A deformable foam and metal clip adheres to the inside of the mask near the top of the top seam to improve sealing and fit around the user's nose, and to enhance the structure of the cavity.

In the center of the vertical front fold, a low restriction one-way valve is attached to allow the user to exhale with almost no restriction. This valve is mounted directly in front of the user's mouth and nose to minimize the amount of used air and moisture that is retained in the mask.

Along each side of the mask are a series of vertical folds to enable pleating. These pleats are unique to the invention as they allow for the effective surface area of filtration media to be increased by 20% or more. The greater surface area substantially reduces restriction for the user to inhale fresh air as his rate of breathing and need for airflow increase with activity.

The geometry of the vertical pleats is defined by fold-lines formed by heat-staking the flat pattern. These heat-staked lines also add the rigidity of the mask structure, helping to maintain the air cavity and exhaust valve location.

The sides of the mask extend along the user's cheeks. Near the user's ear a clip and elastic band are attached for retention and a snug fit to the user's head.

Different combinations of mask materials, pleat sizes, and fastening techniques may be deployed to similar effect. For example: More vertical pleats may be deployed to achieve a lower pressure drop across the mask, different fastening techniques (sewing, adhesives, etc.) may be used instead of heat staking, and a variety of commercially available filtration media can be deployed. Heat staking is the preferred attachment technique.

Glossary

The terms set forth below will have the meanings as defined:

"adequate securement" means not coming loose or becoming separated therefrom under normal use;

"bisect(s)" means to divide into two generally equal parts;

"centrally spaced" means separated significantly from one another along a line or plane that bisects the mask body vertically;

"comprises (or comprising)" means its definition as is standard in patent terminology, being an open-ended term that is generally synonymous with "includes", "having", or "containing". Although "comprises", "includes", "having", and "containing" and variations thereof are commonly-used, open-ended terms, this invention also may be suitably described using narrower terms such as "consists essentially of", which is semi open-ended term in that it excludes only those things or elements that would have a deleterious effect on the performance of the inventive respirator in serving its intended function;

"clean air" means a volume of atmospheric ambient air that has been filtered to remove contaminants;

"contaminants" means particles (including dusts, mists, and fumes) and/or other substances that generally may not be considered to be particles (e.g., organic vapors, et cetera) but which may be suspended in air, including air in an exhale flow stream;

"crosswise dimension" is the dimension that extends laterally across the respirator from side-to-side when the respirator is viewed from the front;

"elastic" means having the ability to return to its initial form or state after being stretched to 100% or more of its initial length;

"exhalation valve" means a valve that opens to allow a fluid to exit a filtering face mask's interior gas space;

"exterior gas space" means the ambient atmospheric gas space into which exhaled gas enters after passing through and beyond the mask body and/or exhalation valve;

"filtering face-piece" means that the mask body itself is designed to filter air that passes through it; there are no separately identifiable filter cartridges or insert-molded filter elements attached to or molded into the mask body to achieve this purpose;

"filter" or "filtration layer" means one or more layers of air-permeable material, which layer(s) is adapted for the primary purpose of removing contaminants (such as particles) from an air stream that passes through it;

"filtering structure" means a construction that is designed primarily for filtering air;

"first side" means an area of the mask body that is laterally distanced from a plane that bisects the mask vertically and that would reside in the region of a wearer's cheek and/or jaw when the respirator is being donned;

"harness" means a structure or combination of parts that assists in supporting the mask body on a wearer's face;

"insert molding" means molding the plastic about at least part of a solid item that has already been placed into the mold;

"integral" means being manufactured together at the same time; that is, being made together as one part and not two separately manufactured parts that are subsequently joined together;

"interior gas space" means the space between a mask body and a person's face;

"line of demarcation" means a fold, seam, weld line, bond line, stitch line, hinge line, and/or any combination thereof;

"mask body" means an air-permeable structure that is designed to fit over the nose and mouth of a person and that helps define an interior gas space separated from an exterior gas space;

"member", in relation to the support structure, means an individually and readily identifiable solid part that is sized to contribute significantly to the overall construction and configuration of the support structure;

"molded" or "molding" means forming into a desired solid shape condition from a previous liquid condition;

"molded about" and "molded thereabout" means placed in contact with a solid item sufficiently through molding to enable adequate securement thereto;

"nose clip" means a mechanical device (other than a nose foam), which device is adapted for use on a mask body to improve the seal at least around a wearer's nose;

"perimeter" means the outer edge of the mask body, which outer edge would be disposed generally proximate to a wearer's face when the respirator is being donned by a person;

"polymeric" and "plastic" each mean a material that mainly includes one or more polymers and that may contain other ingredients as well;

"plurality" means two or more;

"respirator" means an air filtration device that is worn by a person to provide the wearer with clean air to breathe;

"second side" means an area of the mask body that is distanced from a plane line that bisects the mask vertically (the second side being opposite the first side) and that would reside in the region of a wearer's cheek and/or jaw when the respirator is being donned;

"support structure" means a construction that is designed to have sufficient structural integrity to retain its desired shape and to help retain the intended shape of the filtering structure that is supported by it;

"spaced" means physically separated or having measurable distance therebetween; and "transversely extending" means extending generally in the crosswise dimension.

DETAILED DESCRIPTION OF THE DRAWINGS

Figure 1:
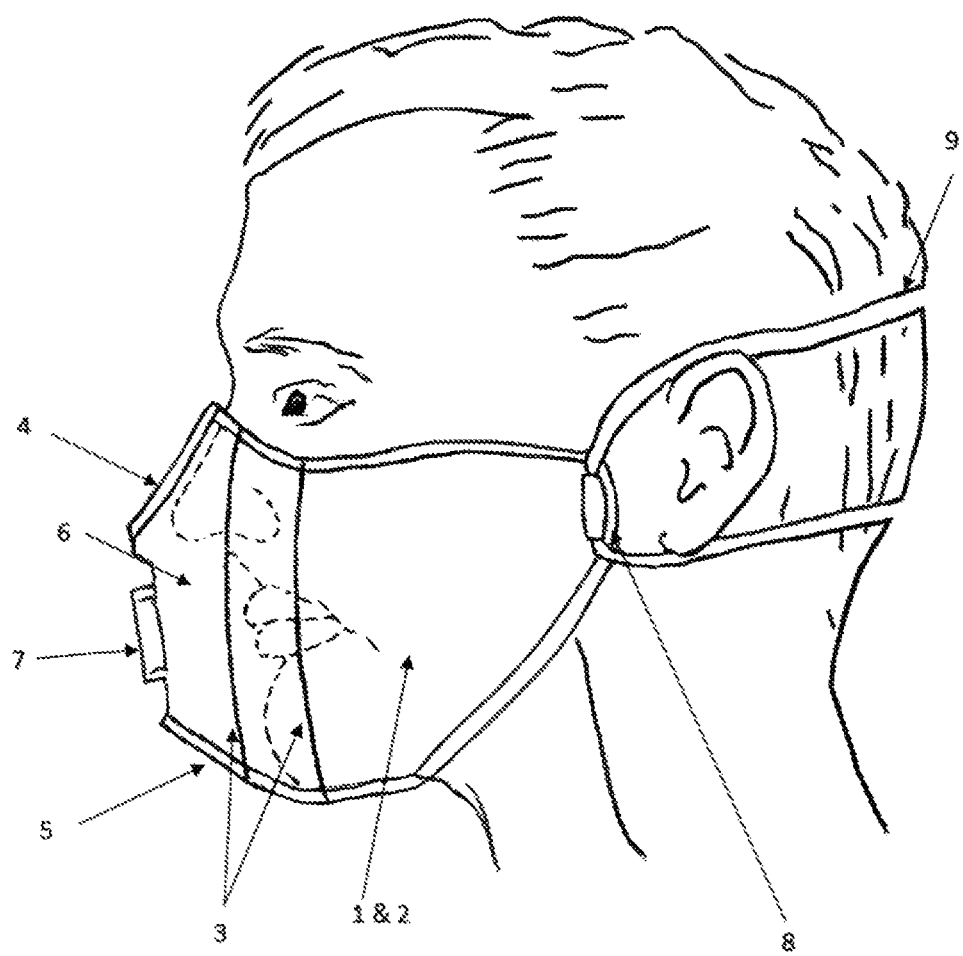
FIG. 1 is a perspective view of the face mask as worn on the user.

FIG. 1: Mask (1) is shown constructed of flat filter material (2) in which pleats (3) have been formed to increase the surface area of filtration media. Top seam (4) and bottom seam (5) create the shape of the mask from the flat sheet of electro-static filter media. This shape is cone-like and conforms to fit a large variety of facial profiles. The two seams also provide structure to the mask, which creates an air cavity (6) between the user and the mask. The ability of these seams to control the size of the cavity is critical to function as it is desirable to minimize the volume of air inside the mask while it is also essential to prevent the surface of the mask from touching the user's mouth or nose. The exhaust valve (7) is positioned directly in front of the user's face and is positioned with the previously mentioned air gap and seams. The elastic band (9) that attaches the mask to the user is secured to the mask by attachment cleats (8).

Figure 2:
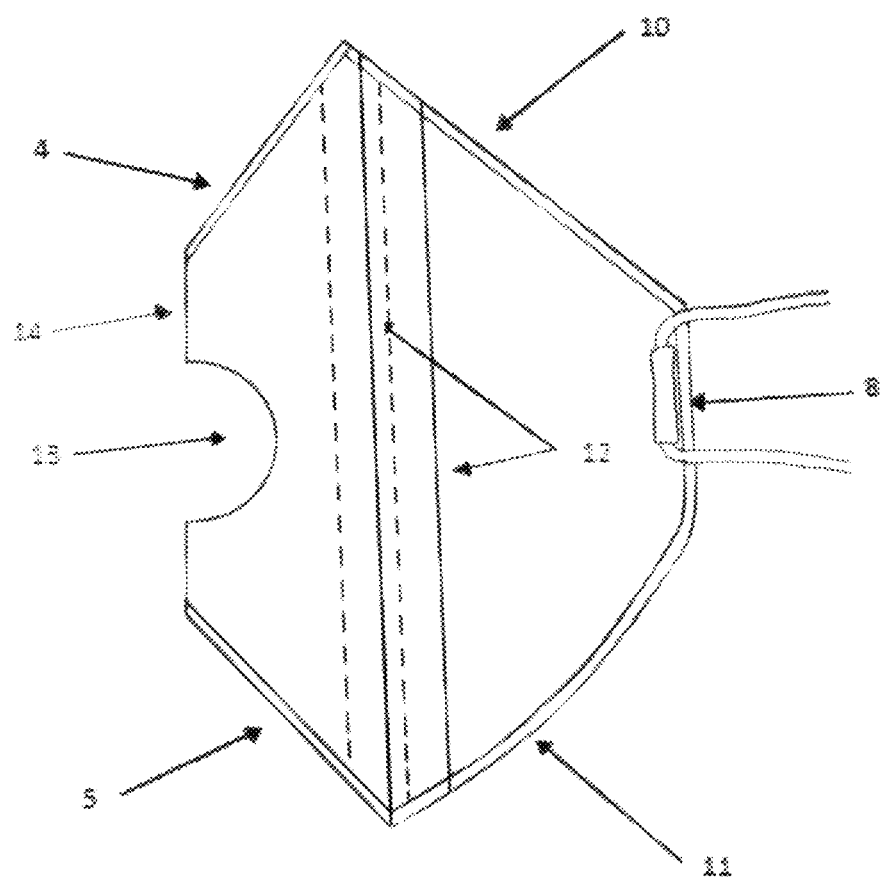
FIG. 2 is an elevational, inside out view of the assembled face mask of FIG. 1, without the exhaust valve installed

FIG. 2: Top and bottom seam (4 & 5) are formed by any one of a number of attachment processes, with heat staking being the preferred process for high volume production. The attachment process is continued along the cheek from the top pleat seam (10) and bottom pleat seam (11) to secure and form the fins of the pleat (12). The shape and alignment of the pleat seams (10 & 11) is critical for both the fit and sealing of the mask. A hole (13) of diameter to support the attachment of the one-way valve is attached. The front edge of the mask (14) is simply folded over until the two seams (4 & 5) come in contact with each other.

Figure 3:
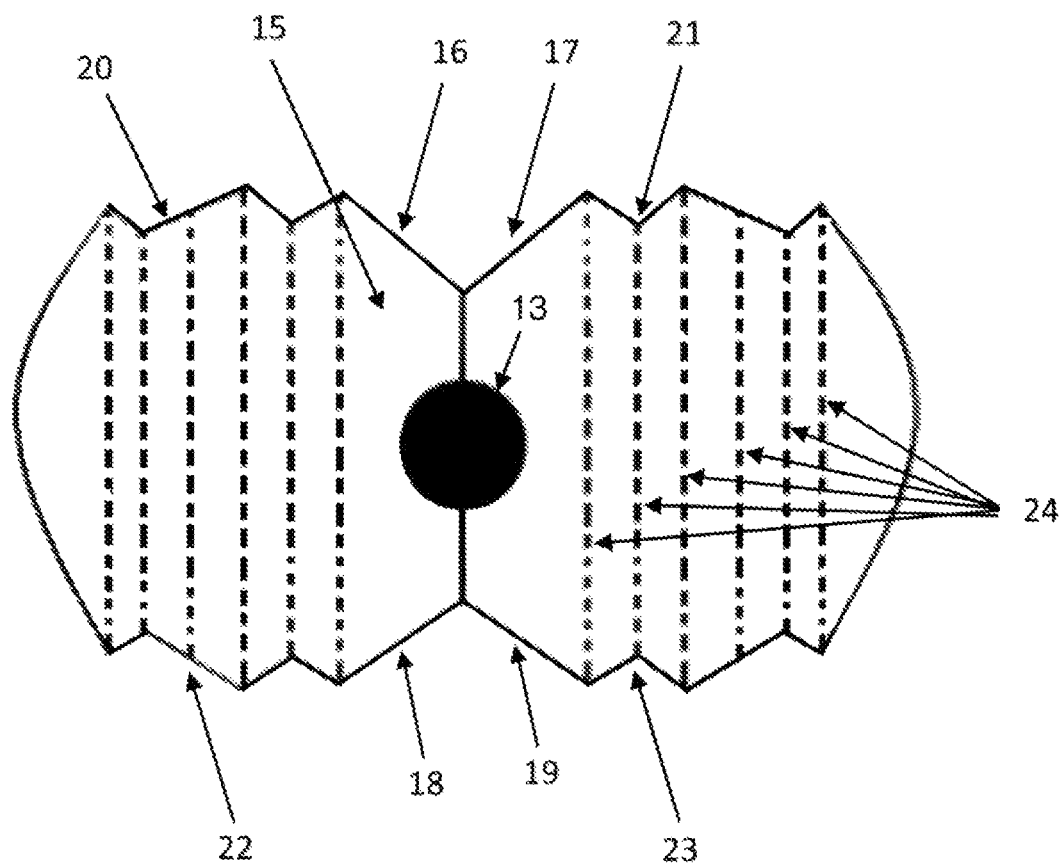
FIG. 3 is a pattern view of the face mask filtration media, shown pre-assembly without valves or retention straps.
Figure 4:
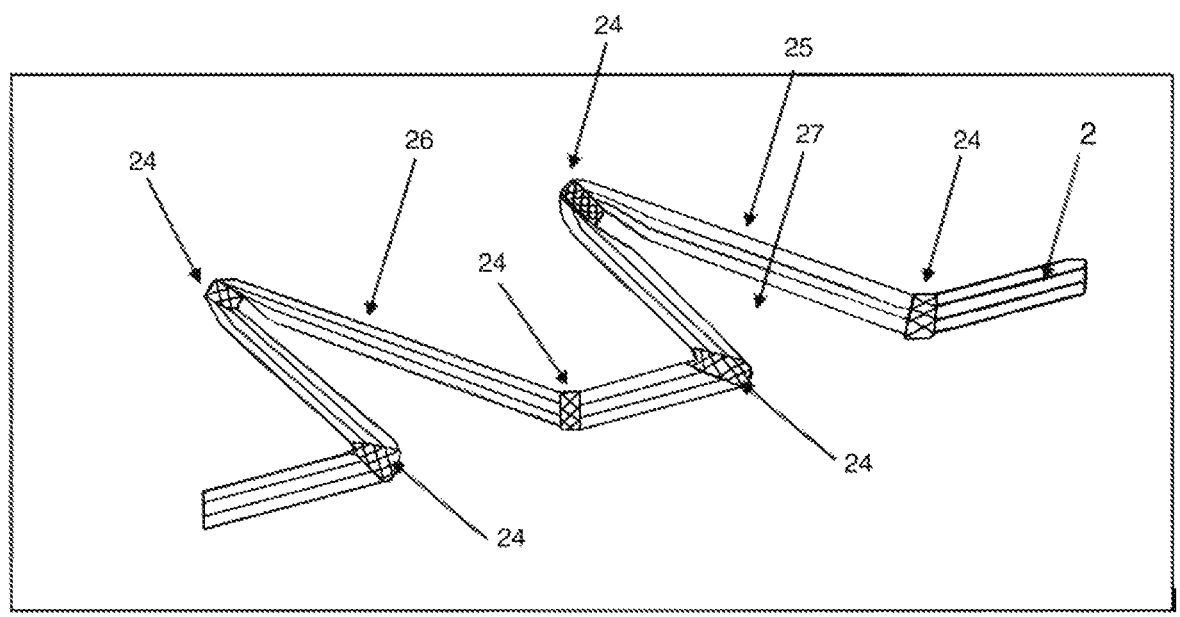
FIG. 4 is a cross sectional diagram of a folded pleat, constructed from a multi-layer flat sheet of filter material.

FIG. 3: The plan view of the flat pattern of filter media (15) is cut to shape to enable the proper shape to form when assembled. Several geometries are critical for the mask to come together easily. These include:

Top edges (16 & 17) which create the top seam (4)
Bottom edges (18 & 19) which meet to form the bottom seam (5)
Pleat profile shapes (20, 21, 22, 23) which must meet when folded to form a continuous edge when assembled
The multiple fold lines (24) are heat-staked or embossed upon the material to ensure precise alignment when assembled The exhaust valve hole (13) is punched into the material prior to assembly FIG. 4: A cross section of the pleats defines the elements critical to increasing the surface area of the multi-layer filter media (2) in order to lower the pressure drop across the mask when the user inhales.

When pulled snug onto the user's face, the pleats (25 & 26) separate enough to allow air flow through and substantially increase the usable surface area of the filtration media while maintaining a small air gap (27) to minimize volume of air trapped within the mask. The folds are defined by the heat-staked fold lines (24) to maintain the geometry of the pleat.

Figure 5:
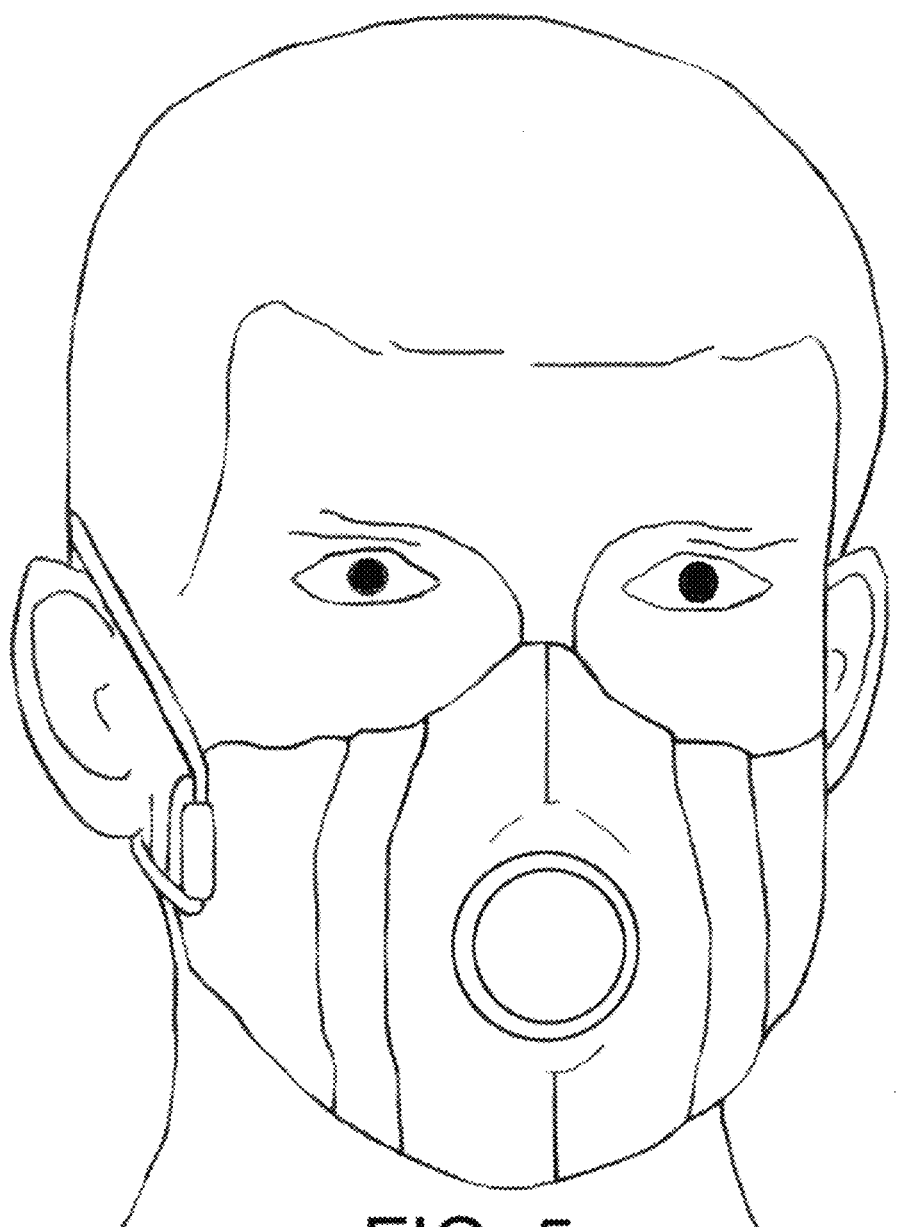
FIG. 5 is a frontal view of the mask being worn by the user.

FIG. 5: A frontal view of the mask as worn by the user.

A 24 mm exhalation valve is attached to the mask body to facilitate purging exhaled air from the interior gas space. The use of an exhalation valve may improve wearer comfort by rapidly removing the warm moist exhaled air from the mask interior. See, for example, U.S. Pat. Nos. 7,188,622, 7,028, 689, and 7,013,895 to Martin et al.; U.S. Pat. Nos. 7,117, 868, 6,854,463, 6,843,248, and 5,325,892 to Japuntich et al.; U.S. Pat. No. 6,883,518 to Mittelstadt et al.; and RE37,974 to Bowers. Essentially any exhalation valve that provides a suitable pressure drop and that can be properly secured to the mask body may be used in connection with the present invention to rapidly deliver exhaled air from the interior gas space to the exterior gas space.

Example

Airflow Resistance to Elevated Inhale and Exhale Rates in Bench Flow Test

The flow and resistance of mask designs stiffness at normal and elevated levels of breathing was conducted in accordance with standards defined in ASTM F 2100. In so doing, test specimens were cut from production 3m N95 filtration media and seams were heat welded to form the mask assembly as described above for testing.

The specimens were prepared and evaluated on a flow-bench of custom construction to support mask testing. Pressure measurements were taken with a RisePro 365BG947677 digital manometer, and airflow was supplied with a Hitichi air compressor.

Targets were established by taking objective measurements on commercially available products with high degrees of customer satisfaction for ease of breathing and comfort during high aerobic rate activities.

Final design demonstrated performance at or below targeted thresholds (where lower is better) for breathing resistance. For inhale at 110 liters per minute, the samples tested were able to demonstrate levels of resistance below 0.35 inches H2O on intake, and 0.25 inches H2O on exhaust.

I claim as my invention:

1. A filter mask comprising:
a flexible mask body constructed from a gas permeable filtration material that is shaped to cover portions of a face of a user, the flexible mask body comprising:
a top body portion that covers one or more contours of a nose of the user when worn;
a bottom body portion that covers one or more contours of a chin of the user when worn;

a mid-body portion extending between the top body portion and the bottom body portion, wherein the mid-body portion covers a right cheek and a left cheek of the user and extends from the right cheek to the left cheek;

a plurality of vertical pleats, each of the plurality of vertical pleats having a top end and a bottom end and extending from the top body portion to the bottom body portion, wherein each of the plurality of pleats is folded closed and fixed at the top and the bottom end, and each pleat being expandable in the mid-body portion;

a one-way exhale valve positioned near a center of the mid-body portion;

a first vertical seam positioned at a centerline of the top-body portion and a second vertical seam positioned at a centerline of the bottom-body portion, wherein the first vertical seam and the second vertical seam are positioned to create a semi-rigid chamber wherein the first vertical seam and second vertical seam do not extend through the mid-body portion of the flexible mask body; and a retainer system to elastically secure the filter mask body to the face of the user, the retainer system consisting of at least one strap fastened to a right side and a left side of the filter mask body.

2. The filter mask of claim 1, wherein the semi-rigid chamber of the mask body with the exhale valve fixed to a hole in the mid-body portion of the mask creates a sealed air cavity between the mask body and the face of the user with a gap between the mask body and the mouth and the nose of the user.

3. The filter mask of claim 1 wherein the flexible mask body is constructed by folding and joining a single sheet of the gas permeable filtration material.

4. The filter mask of claim 3 wherein the semi-rigid chamber positions the exhale valve and the mask body a prescribed distance from the mouth and the nose of the user.

5. The filter mask of claim 3 wherein the installation of the exhale valve into the semi-rigid chamber expands the vertical pleats in the mid-body section of the flexible mask body.

6. The filter mask of claim 1 wherein the placement of the vertical pleats aid the semi-rigid chamber in articulating to the contours of the nose and the contours of the chin and other features of the shape of the face of the user.

7. A method of constructing a flexible mask body from a single contiguous sheet of permeable filtration material, the method comprising:

cutting a pre-aligned shape from the single sheet of permeable filtration material to form a cut sheet;

defining fold lines from a top portion to a bottom portion of the single sheet of permeable filtration material;

folding the cut sheet of permeable filtration material along its defined fold lines to form one or more vertical pleats; and folding across at a centerline, joining the folded sheet at the centerline as a seam, and permanently closing the vertical pleats by bonding at the top portion and the bottom portion of the flexible mask body.

8. The method of claim 7, wherein the folding and the joining of the single sheet of permeable filtration material provides structure to the body of the filter mask to form a semi-rigid chamber.

9. The method of claim 7, wherein the folding and the joining of the single sheet of permeable filtration material hold the body of the filter mask in an ovular shape contouring the face of the user, providing stability to the seal on the face of the user.

10. The method of claim 7, wherein the semi-rigid chamber is defined by one or more geometries cut into the single contiguous sheet of permeable filtration material when joined at the centerline of the top portion and the bottom portion of the flexible mask body.

* * * * *